United States Patent [19]

Schaefer-Luederssen et al.

[11] Patent Number: 4,594,456
[45] Date of Patent: Jun. 10, 1986

[54] RACEMIC AND OPTICALLY ACTIVE 3-HYDROXY-ALPHA-CYCLOCITRAL, ITS ACETALS AND OPTICALLY ACTIVE 3-OXO-ALPHA-CYCLOCITRAL ACETALS, AND THEIR PREPARATION

[75] Inventors: Ulrich Schaefer-Luederssen; Hagen Jaedicke, both of Ludwigshafen; Joachim Paust, Neuhofen; Manfred Eggersdorfer, Mannheim, all of Fed. Rep. of Germany

[73] Assignee: BASF Aktiengesellschaft, Ludwigshafen, Fed. Rep. of Germany

[21] Appl. No.: 572,239

[22] Filed: Jan. 20, 1984

[30] Foreign Application Priority Data

Jan. 20, 1983 [DE] Fed. Rep. of Germany ....... 3301718
Nov. 17, 1983 [DE] Fed. Rep. of Germany ....... 3341463

[51] Int. Cl.[4] .................................. C07C 47/267
[52] U.S. Cl. ................................ 568/447; 568/446; 568/378; 568/591; 549/453; 549/374
[58] Field of Search ............... 568/446, 447, 591, 378; 549/453, 374

[56] References Cited

U.S. PATENT DOCUMENTS

| | | | |
|---|---|---|---|
| 3,068,292 | 12/1962 | Reedy et al. | 568/447 |
| 3,184,516 | 5/1965 | Chechak et al. | 568/447 |
| 3,410,908 | 11/1968 | Rowland et al. | 568/378 |
| 3,514,489 | 5/1970 | Lermberg | 568/591 |
| 3,661,997 | 5/1972 | Sunmatis et al. | 568/447 |
| 4,152,355 | 5/1979 | Traas | 568/591 |
| 4,233,464 | 11/1980 | Baumann et al. | 568/591 |

OTHER PUBLICATIONS

Kaiser et al, Helv Chemical Acta, vol. 61, pp. 373–82 (1978).
Buchecker et al, Helv Chimica Acta, vol. 57, pp. 631–56 (1974).
Duquenois, Chem. Abst, vol. #79, #45885q (1973).
Chem. Abst, vol. #95, #132362r (1980).

*Primary Examiner*—James H. Reamer
*Attorney, Agent, or Firm*—Oblon, Fisher, Spivak, McClelland & Maier

[57] ABSTRACT

3-Hydroxy-α-cyclocitral derivatives of the general formula I

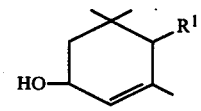

where $R^1$ is

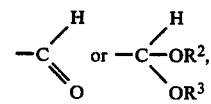

wherein $R^2$ and $R^3$ can be identical or different and are each straight-chain or branched alkyl of 1 to 6 carbon atoms, or $R^2$ and $R^3$ together form an ethylene or propylene group which can be substituted by methyl or ethyl, processes for their preparation and their use for the preparation of safranal and 3-hydroxy-β-cyclocitral, as well as optically active - cyclocitral derivatives of the general formulae A and B

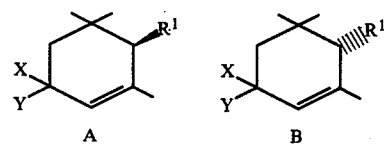

where $R^1$ is

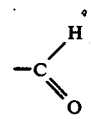

if X is hydrogen and Y is OH, but is otherwise

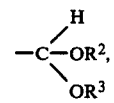

where $R^2$ and $R^3$ have the above meanings, and X and Y together are oxygen, or X is hydrogen if Y is OH, and a process for the preparation of optically active 3-oxo-α-cyclocitral acetals, wherein a mixture of the corresponding racemic 3-oxo-α-cyclocitral acetals is separated into the optically active compounds by chromatography over a suitable chiral adsorbent. The novel compounds open up a novel advantageous route to optically active 3-hydroxy-β-cyclocitrals, which are desirable because they are important intermediates for carotinoids identical to the natural products.

17 Claims, No Drawings

RACEMIC AND OPTICALLY ACTIVE 3-HYDROXY-ALPHA-CYCLOCITRAL, ITS ACETALS AND OPTICALLY ACTIVE 3-OXO-ALPHA-CYCLOCITRAL ACETALS, AND THEIR PREPARATION

FIELD OF THE INVENTION

The present invention relates to 3-hydroxy-α-cyclocitral derivatives of the general formula I

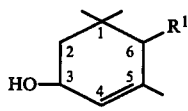

where $R^1$ is

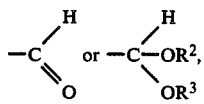

wherein $R^2$ and $R^3$ can be identical or different and are each straight-chain or branched alkyl of 1 to 6 carbon atoms, or $R^2$ and $R^3$ together form an ethylene or propylene group which can be substituted by methyl or ethyl, and to optically active α-cyclocitral derivatives of the general formulae A and B

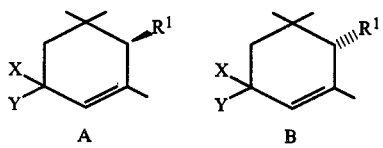

wherein $R^1$ is

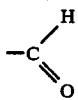

if X is hydrogen and Y is OH, but is otherwise

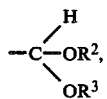

where $R^2$ and $R^3$ have the above meanings, and X and Y together are oxygen, or X is hydrogen if Y is OH, and to processes for their preparation and their use for the preparation of safranal and 3-hydroxy-β-cyclocitral or of optically active 3-hydroxy-β-cyclocitral acetals, which are important intermediates for the preparation of desirable optically active carotinoids which are identical to the natural products, eg. (3R, 3'R)-zeaxanthin or (3R, 3'R, 6'R)-lutein.

DESCRIPTION OF THE PRIOR ART

The stated carotinoids are important natural dyes which occur in plants and algae. Since the isolation of these dyes from the natural source is complicated and expensive and falls far short of covering the demand, many attempts have been made to prepare these compounds by a completely synthetic route. To date, the starting compounds required for this purpose, which contain terpenoid structural elements possessing oxygen functional groups, have been very expensive to prepare and are often obtained in unsatisfactory yields. For example, Loeber et al. (J. Chem. Soc. (C) (1971), 404–408), describe a synthesis of zeaxanthin by the following route:

The ketone 1 prepared from isophorone is reacted with a Grignard reagent prepared from but-3-yn-2-ol to give the diol 2, from which the dihydroxyketone 3 is formed by eliminating the ethylenedioxy protective group. The dihydroxyketone 3 can be reduced with lithium aluminum hydride to the triol 4, which can be reacted with acetic anhydride in pyridine to give the acetate 5. Dehydration of 5 with phosphoryl chloride in pyridine gives the enyne diacetate 7, which can be reduced with lithium aluminum hydride to the enynediol 6 and, when the reaction is carried out under more stringent conditions, to 3-hydroxy-β-ionol. Selective oxidation of 8 with manganese dioxide gives 3-hydroxy-β-ionone 9. Reaction of the latter with vinyl magnesium bromide gives the vinyl alcohol 10, which, when treated with triphenylphosphonium bromide, forms the Wittig reagent 11. When the latter is heated with the dialdehyde 12 in 1,2-epoxybutane, zeaxanthin 14 is obtained in good yield. Condensation of the Wittig salt 11 with ($C_{25}$-)-β-apo-12'-carotenal 16 in 1,2-epoxybutane gives β-cryptoxanthin 18, or condensation of 11 with racemic ($C_{25}$-)-α-apo-12'-carotenal gives zeinoxanthin 17. Equation 1 below illustrates the synthetic route described:

Equation 1:

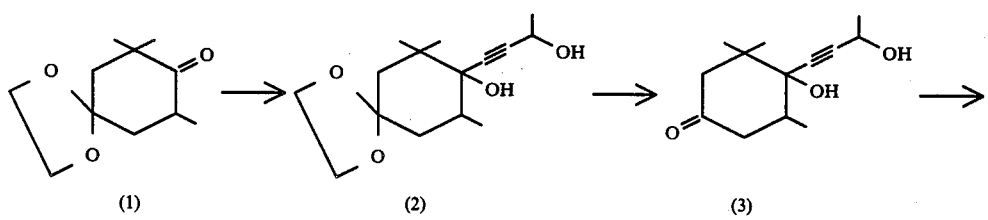

-continued

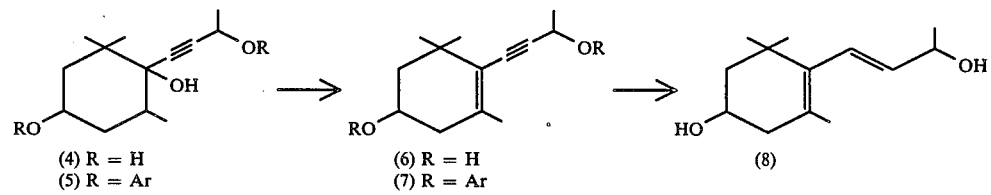
(4) R = H
(5) R = Ar (6) R = H
(7) R = Ar (8)

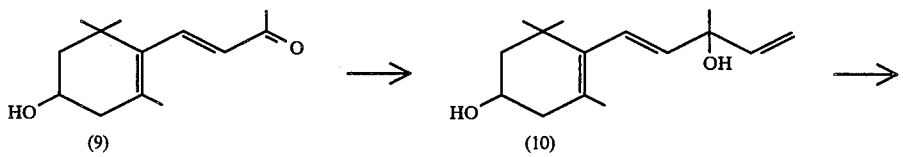
(9)

(10)

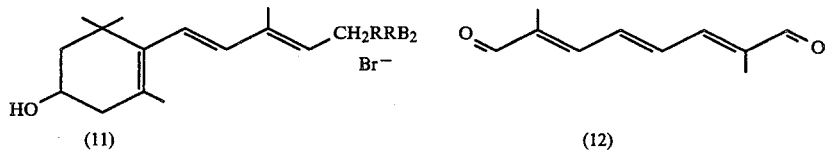
(11)

(12)

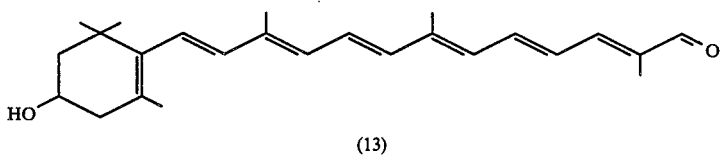
(13)

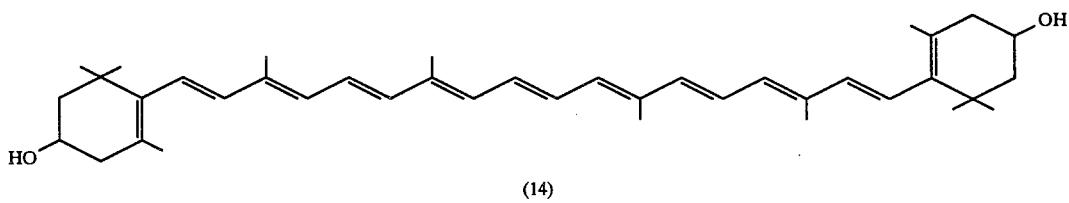
(14)

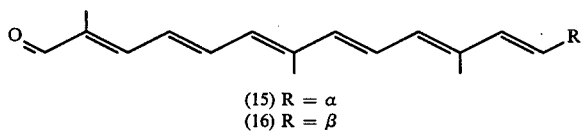
(15) R = α
(16) R = β

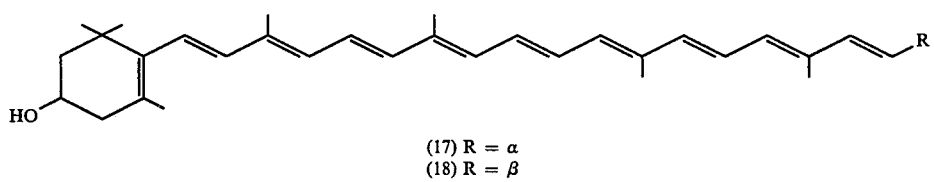
(17) R = α
(18) R = β

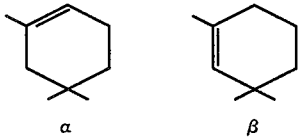
α    β

As is evident from the description, the preparation of the desirable carotinoids starting from 3-hydroxy-β-ionone 9 is very simple and advantageous, but the route to the hydroxy-β-ionone 9, because it involves a larger number of complicated reaction stages, such as repeated reaction with lithium aluminum hydride and the heterogeneous oxidation of 8 with manganese dioxide, is unsuitable for industrial production.

SUMMARY OF THE INVENTION

The present invention to provide a novel more advantageous route for the preparation of 3-hydroxy-β-ionone.

The α-cyclocitral derivatives of the general formula are obtainable in a relatively simple manner and open up a novel industrially more advantageous route to synthesizing 3-hydroxy-β-ionone. The 3-hydroxy-β-cyclocitral acetals of the formula Ia furthermore provide a novel advantageous route to safranal, which has a desirable aroma.

DESCRIPTION OF THE PREFERRED EMBODIMENTS

The present invention accordingly relates to the compounds of the formula I which have been defined above, and their use for the preparation of 3-hydroxy-β-ionone and safranal, as well as to a process for the preparation of 3-hydroxy-β-cyclocitral derivatives of the general formula I

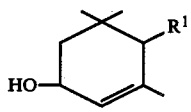

wherein $R^1$, $R^2$ and $R^3$ have the meanings stated at the outset,
wherein
(a) the corresponding trimethylcyclohexene acetal of the general formula II

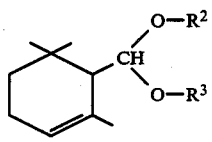

is oxidized with a suitable oxidizing agent, preferably with oxygen and tert.-butyl hydroperoxide in the presence of a rhodium compound, in particular or rhodium trichloride hydrate or rhodium-tristriphenylphosphonium chloride, or with tert.-butyl hydroperoxide in the presence of Cu(II) acetylacetonate, or with di-tert.-butyl chromate as a suitable oxidizing agent, to the 3-oxo-α-cyclocitral acetal of the general formula III

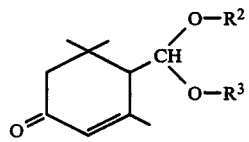

(b) this is reduced with a suitable reducing agent, preferably with sodium borohydride in the presence of a cerium(II) compound, or with diisobutyl aluminum hydride, or with lithium tri-tert.-butoxy-aluminum hydride as a suitable reducing agent, to the 3-hydroxy-α-cyclocitral acetal of the general formula Ia

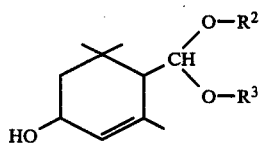

and, if required,
(c) this is hydrolyzed in the presence of an organic or inorganic acid in an aqueous organic solvent, preferably in the presence of p-toluenesulfonic acid in about 70 vol.% aqueous acetone.

The trimethylcyclohexene acetals II required as starting materials for the novel process are obtainable in a relatively simple manner by acetalization of α-cyclocitral under conventional conditions, for example with trimethyl orthoformate in accordance with Bull. Chem. Soc. Jap. 50 (5) (1977), 1161–1168, or with an appropriate glycol, with elimination of water in the presence of p-toluenesulfonic acid, with toluene as an entraining agent. Hence, the synthetic route to the desirable 3-hydroxy-β-ionone and therefore to carotinoids, eg. zeaxanthin, is the simple one below:

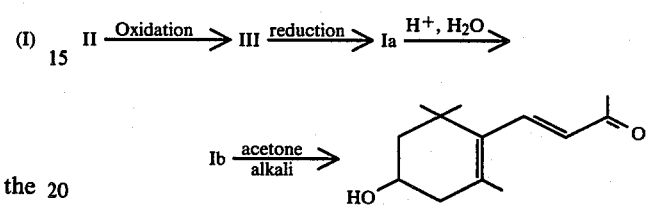

Some of the 3-oxo-α-cyclocitral acetals of the general formula III which occur as intermediates in the novel process have recently been described (cf. Takazawa et al., Bull. Chem. Soc. Jap. 55 (1982), 1907–1911); however, for several reasons, the synthetic route for these compounds which is described in the stated publication and starts from isophorone is not very advantageous for an industrial-scale process.

The individual stages of the novel process are described in detail below.

With regard to (a):

The oxidation of the α-cyclocitral acetals II to the 3-oxo-α-cyclocitral acetals III can be carried out with various oxidizing agents. For example, II can be converted to III using tert.-butyl hydroperoxide and oxygen or air in the presence of rhodium-tristriphenylphosphonium chloride as a catalyst. The tert.-butyl hydroperoxide is used in general in an amount such that the volume ratio of hydroperoxide to II is from 1:5 to 1:0.2, preferably about 1:1. The reaction temperature can be from 40° to 110° C., but is preferably from 60° to 90° C. The reaction can be carried out in the absence of a solvent, but it is also possible to dilute the reaction medium with a solvent which is inert under the reaction conditions, eg. tert.-butanol, chlorobenzene or xylene. The reaction velocity with pure oxygen is higher than that with air, but it is also possible to dilute the oxidizing gas with an inert gas if this is desirable for safety reasons. The amount of catalyst can likewise be varied within wide limits. About 1 mole % is preferably used, but the desired product is still obtained if 0.1 mole % is employed. A typical procedure can be found in the paper by Reuter et al (J. Org. Chem. 43 (1978), 2438–2442), in which the oxidation of various cycloalkenes is described. Furthermore, we have found, surprisingly, that RhCl$_3$.3H$_2$O can be used instead of the triphenylphosphine complex of rhodium in the novel reaction. Under otherwise identical conditions, the amount of catalyst can be reduced to 0.2–0.02 mole % when RhCl$_3$.3H$_2$O is used.

Another possible method of oxidizing II to III is to use tert.-butyl hydroperoxide as the oxidizing agent and Cu(II) acetylacetonate as a catalyst. Air or oxygen need not be used in this case, and it is even advantageous to carry out the reaction under a protective gas atmosphere.

The tert.-butyl hydroperoxide is used in general in an amount of from 2 to 30, preferably about 10, moles per mole of II, and the acetylacetonate is used in an amount of from 1 to 100, preferably about 10, mole %, based on II. The reaction temperature can be from 40° to 120° C., and the reaction time from 6 to 24 hours, depending on the reaction temperature. This process is described by Kimura and Muto (cf. *Chem. Pharm. Bull. Jap.* 29 (1981), 35–42) for the oxidation of cholesteryl acetate.

The oxidation of II to III can furthermore be carried out using di-tert.-butyl chromate as the oxidizing agent. This is used in general in an amount of from 1 to 10, preferably about 2–4, moles per mole of II. The reaction is advantageously carried out as follows: a solution of the chromate in an inert solvent, eg. CCl₄, is added slowly to a solution of II in acetic anhydride, and the stirred reaction mixture is heated for about 1–30, preferably about 20–24, hours at from 40° to 80° C., preferably at about 60°–65° C. This process is described by Könst and Apeldoorn (cf. *Synth. Commn.* 10, Part 12 (1980), 899–904) for the oxidation of α-ionene.

Depending on the reaction conditions, the novel cyclohexenones II are obtained in yields of from 30 to 70%.

It is surprising that, under the conditions described, the hydrogen atoms on carbon 3 are subjected to oxidative attack with high selectivity. Since there are three different groups of allylhydrogen atoms in II, the formation of complicated product mixtures was to be expected. This expectation was reinforced by the fact that, under corresponding reaction conditions, Reuter et al (loc. cit.) also observed double-bond shifts which gave rise to the formation of various oxidation products. Moreover, it was to be expected that, under the reaction conditions, the acetal group would be destroyed. In fact, the corresponding saturated acetals decompose under the stated reaction conditions in a short time to form 2,2,6-trimethylcyclohexanecarboxylic acid (cf. comparative example).

Regarding (b):

The conversion of the resulting 3-oxo-α-cyclocitral acetals III to the 3-hydroxy-α-cyclocitral acetals Ia is carried out in a conventional manner, so that detailed descriptions are unnecessary. It can be carried out, for example, with sodium borohydride in the presence of a cerium(III) salt, or with another mild reducing agent, eg. diisobutyl-aluminum hydride or lithium tri-tert.-butoxy-aluminum hydride, in a conventional manner.

The alcohols Ia can be obtained in the cis or trans form or as a mixture, depending on the reaction conditions. However, with regard to further use, the isomer composition of Ia is of minor importance.

Regarding (c):

The novel 3-hydroxy-α-cyclocitral acetals Ia can be readily hydrolyzed with a dilute acid in a water-miscible inert solvent, eg. methanol, acetone or tetrahydrofuran, to give 3-hydroxy-α-cyclocitral of the formula Ib. If the acid-catalyzed hydrolysis is carried out in an anhydrous medium, the product obtained is not 3-hydroxy-α-cyclo-citral but its dehydration product, ie. safranal (IV). For this reason, the hydrolysis of Ia to Ib must be carried out using a solvent which contains from 1 to 80, preferably from 20 to 70, % by weight of water. Suitable acids for this reaction are all moderately strong or strong non-oxidizing inorganic or organic acids which are conventionally employed for acid-catalyzed hydrolyses. Examples include mineral acids, eg. sulfuric acid or phosphoric acid, organic acid, eg. p-toluenesulfonic acid or citric acid, and acidic cation exchangers. The conventional amounts of acid are used, ie. from about 0.1 to 10, preferably from 0.5 to 1.5, mole %. The hydrolysis is preferably carried out at room temperature, but also takes place at higher temperatures, eg. about 50° C., or lower temperatures, eg. about 0° C. It is particularly advantageous to use p-toluenesulfonic acid in about 70 vol. % aqueous acetone.

The conversion of Ia to safranal (IV) is carried out under the conditions described under (c) for the hydrolysis, but in an anhydrous solvent.

The isomerization of 3-hydroxy-α-cyclocitral (Ib) to 3-hydroxy-β-cyclocitral (V) is carried out in the presence of an alkali metal hydroxide, eg. NaOH or KOH, or in the presence of an alkali metal alcoholate, in particular sodium methylate.

Advantageous organic solvents for this isomerization are alkanols, eg. methanol or ethanol, and acetone. With acetone as the solvent and with relatively long reaction times (eg. 3 hours), the condensate, 3-hydroxy-β-ionone, can be isolated directly; this can be converted to the naturally occurring carotinoid zeaxanthin in the manner described by Loeber et al (loc. cit.).

The alkali metal compounds are used in these isomerizations in general in amounts of from 0.5 to 2 moles, based on cyclocitral employed. A synthetic route to a (3R, 3'R)-zeaxanthin which is identical to the natural product is described by, for example, A. Rüttimann and H. Mayer in *Helv. Chim. Acta* 63 (1980), 1456–1462; this route is as follows:

Safranal (1) is reduced with diisobutyl-aluminum hydride to safranol (2), which is protected by converting it with isopropenyl methyl ether to the acetal (3). After oxidation with NaOH/H₂O₂ followed by acidic hydrolysis, the optically active (3R)-3-hydroxy-β-cyclogeraniol (4) can be obtained in a yield of 30%, using the chiral hydrogenating reagent (+)-diisopinocamphenylborane prepared in situ from (−)-alpha-pinene and borane-dimethyl sulfide complex. With (+)-alpha-pinene, the enantiomeric compound (3s)-3-hydroxy-β-cyclogeraniol is formed. Selective oxidation of (4) gives the desired product, ie. (3R)-3-hydroxy-β-cyclocitral (5). Reaction with acetone in the presence of sodium methylate leads to (3R)-3-hydroxy-β-ionone (6), which reacts with two equivalents of vinyl magnesium bromide to give the diol (7). This is converted to the phosphonium salt (8) with methanolic HCl. A Wittig reaction with a conventional symmetric C₁₀-dialdehyde finally gives all-E-(3R,3'R)-zeaxanthin (9). The quality of the alpha-pinene employed as a reagent is critical for the optical purity of the end product.

This synthetic route is illustrated by the scheme below:

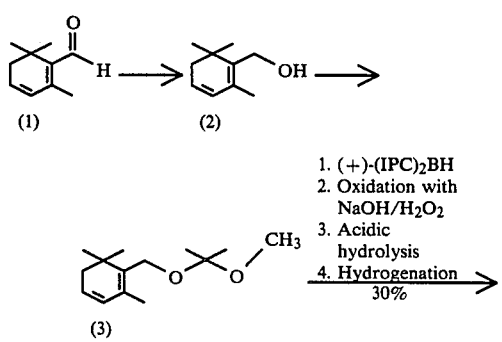

-continued

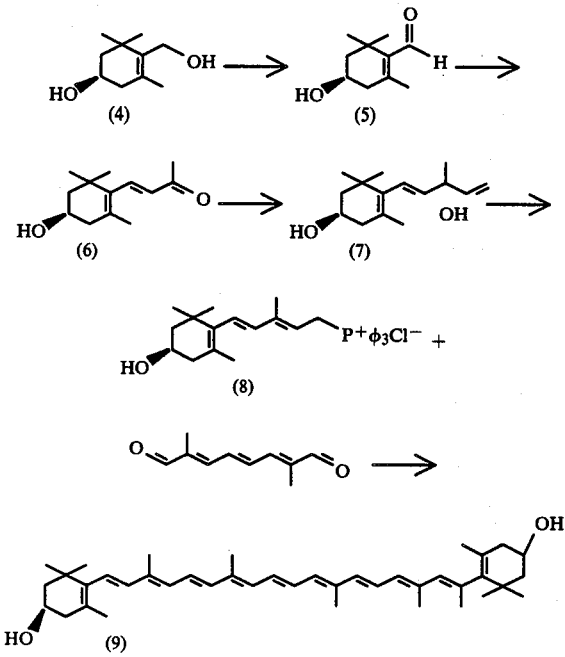

As can be seen from the description, the preparation of the desired carotinoid zeaxanthin from (3R)-3-hydroxy-β-cyclocitral is very simple and advantageous. However, because the starting materials are not readily available and the reaction steps are complicated, the route described for the preparation of (3R)-3-hydroxy-β-cyclocitral is unsuitable for industrial use.

It is an object of the present invention to provide a novel, more advantageous route for the preparation of optically active 3-hydroxy-β-cyclocitral.

Resolution of the racemate of the relatively readily decomposable 3-hydroxy-α-cyclocitral acetals or of the free aldehydes cannot be carried out industrially in an advantageous manner.

The 3-oxo-α-cyclocitral acetals, which can be obtained readily and in good yields, possess an asymmetrically substituted carbon atom (in position 6) and therefore occur in the form of two optically active isomers; hence, it would in principle be possible to use optically active 3-oxo-β-cyclocitral acetals as starting compounds for the desired optically active 3-hydroxy-β-cyclocitral.

However, the compounds do not possess any suitable functional groups which permit a simple separation into the two optically active isomers with the aid of diastereomeric compounds. For this reason, it was necessary to find alternative methods for separating the optical isomers. One such method consists in principle in chromatographing the racemic mixtures over optically active adsorbents.

These optically active adsorbents can consist of natural polymers, derivatized natural polymers or special synthetic polymers.

However, according to the literature, a precondition for such a chromatographic separation is the possibility of forming hydrogen bonds (cf. G. Blaschke, *Angew. Chemie* 92 (1980), 14–25), the possibility of donor-acceptor interactions (cf. W. H. Pirkle et al, *J. Org. Chem.* 44 (1979), 1957–1960) or the presence, in the proximity of the chiral center, of preferably unsubstituted phenyl radicals (cf. G. Hesse and R. Hagel, *Chromatographia* 9 (1976), 62–68); hence, appropriately substituted compounds must be available.

We have found, surprisingly, that 3-oxocyclocitral acetals can be resolved with their optical isomers by chromatography over such optically active adsorbents.

We have found that the separation over derivatized cellulose, in particular over triacetylated natural cellulose, as obtained by, for example, the Schering process by acetylation of cellulose in benzene with perchloric acid as a catalyst, or in toluene with sulfuric acid as a catalyst (cf. Houben-Weyl, Methoden der Organischen, Chemie, 4th Edition, XIV/2, page 875, line 5 et seq.), is very successful when lower alkanols are used as eluting agents. Suitable alkanols for this purpose are methanol, ethanol, propanol, isopropanol, n-butanol and isobutanol, as well as mixtures of these.

The present invention accordingly also relates to a process for the preparation of optically active 3-oxo-α-cyclocitral derivatives of the general formulae A III and B III, wherein a racemic mixture of the corresponding 3-oxo-α-cyclocitral acetals is resolved into the optically active acetals by chromatography over a suitable chiral adsorbent, preferably over derivatized cellulose. Particularly advantageously, the 3-oxo-α-cyclocitral acetals are separated over triacetylated cellulose with a lower alkanol as the eluting agent.

The process described above gives the dextrorotatory as well as the levorotatory acetal. If, for reasons of further processing, only one of the two forms is desired, the undesired form can be converted to the racemate again in a simple manner by isomerization with a base in an alkanol as the solvent.

The racemate recovered can once again be subjected to the chromatographic separation. By recycling, the total amount of racemic 3-oxo-α-cyclocitral acetal can be converted to either optically active Ia or optically active Ib. This particular economic advantage is further reinforced by virtue of the fact that no expensive reagents are consumed.

The present invention furthermore relates to a process for the preparation of optically active 3-hydroxy-α-cyclocitral derivatives of the general formulae A and B

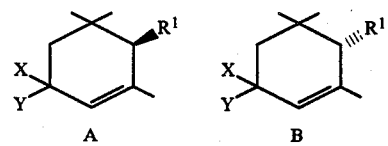

where X, Y, $R^1$, $R^2$ and $R^3$ have the meanings given in claim 1, wherein (a) corresponding trimethylcyclohexene acetal of the general formula II

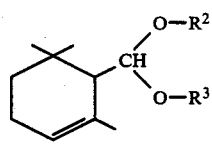

is oxidized with a suitable oxidizing agent to a 3-oxo-α-cyclocitral acetal of the general formula III

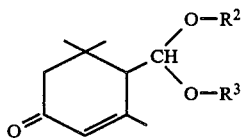

(aa) this is separated, as described above, into the optically active 3-oxo-α-cyclocitral acetals of the formulae A III and B III

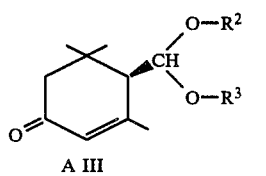 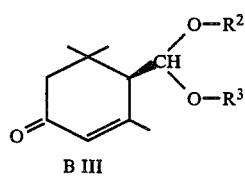

A III    B III (b) these are, if desired, reduced stereoselectively with a suitable reducing agent to optically active trans- or cis-3-hydroxy-α-cyclocitral acetals of the general formulae A′I and B′I

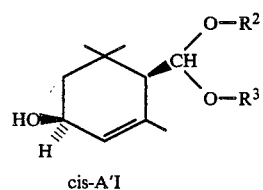 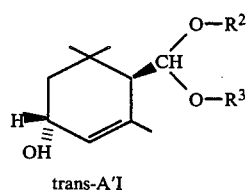

cis-A′I    trans-A′I

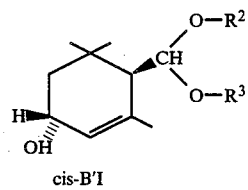 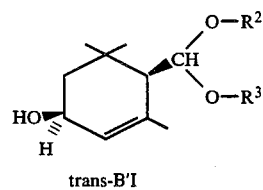

cis-B′I    trans-B′I and, if desired, (c) these are hydrolyzed in the presence of an organic or inorganic acid in an aqueous organic solvent to give the optically active 3-hydroxy-α-cyclocitrals of the formulae trans- and cis-A″I and B″I

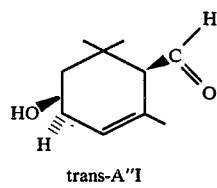 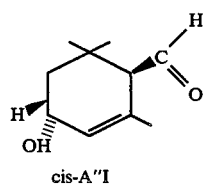

trans-A″I    cis-A″I

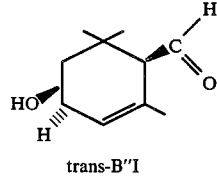 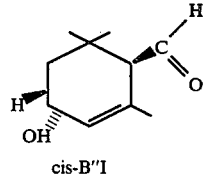

trans-B″I    cis-B″I

Suitable reducing agents for step (b) are sodium borohydride in the presence of a cerium(III) compound, and diisobutyl-aluminum hydride and lithium tri-tert.-butoxy-aluminum hydride. Preferred reaction conditions for steps (b) and (c) are the same as those described above for steps (b) and (c) for the corresponding racemic compounds.

The present invention furthermore relates to the use of optically active 3-hydroxy-α-cyclocitrals of the formulae A″I and B″I for the preparation of optically active 3-hydroxy-β-cyclocitrals of the formulae Va and Vb

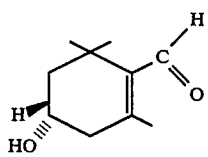 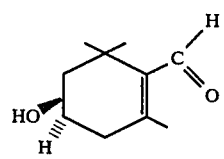

Va    Vb by isomerization in the presence of an alkali metal hydroxide or alkali metal alkoxide in a suitable organic solvent.

EXAMPLES

Example 1

Preparation of 3-oxo-cyclocitral dimethyl acetal (A) Oxidation with $O_2$ and tert.-butyl hydroperoxide in the presence of $RhCl_3.3H_2O$ A mixture of 50 ml (47.6 g; 0.238 mole) of α-cyclocitral dimethyl acetal, 50 ml of 80% strength tert.-butyl hydroperoxide, 200 mg of $RhCl_3.3H_2O$ and 2 g of $NaHCO_3$ was gassed with 5 liters/hour of oxygen for 25 hours at 60° C. The reaction mixture was washed with twice 40 ml of water, the aqueous phase was extracted with methyl tert.-butyl ether (MTB), and the organic phases were combined, and dried over $MgSO_4$. In a micro thin-film evaporator, the crude product was degassed under 0.6 mbar and freed from low-boiling components. The residue (46 g) was taken up in 60 g of peanut oil, and the solution was distilled under 0.01 mbar at 130° C. 36 g of a 71% strength 3-oxo-α-cyclocitral dimethyl acetal were obtained. This corresponds to a yield of 50.1% of theory.

(B) Oxidation with $(tert.-butyl)_2CrO_4$ (a) Preparation of $(tert.-butyl)_2CrO_4$ A solution of 138 g (1.38 moles) of $CrO_3$ in 230 ml of water was added dropwise to 246 g of tert.-butanol at room temperature, and the reaction mixture was stirred at this temperature for 1 hour. The resulting solution was extracted twice with 700 ml of carbon tetrachloride, and the organic phase was washed with 250 ml of $H_2O$ and then evaporated down to about 900 ml in a rotary evaporator at from 20° to 30° C.

(b) Oxidation 700 ml of the solution prepared as described in (Ba) were added dropwise to a solution of 165 g (0.83 mole) of α-cyclocitral dimethyl acetal in 180 ml of acetic anhydride in the course of 1¼ hours at 60° C., after which the reaction mixture was stirred at from 60° to 65° C. for 22 hours. It was cooled and then filtered under suction over silica gel, the residue was washed with 1 liter of $CCl_4$, and the filtrate was washed neutral with 300 ml of saturated $NaHCO_3$ solution, dried over $MgSO_4$ and evaporated down to give 169 g of crude product.

Distillation at from 63° to 80° C. under 0.01 mbar gave 68 g of a 95% pure 3-oxo-α-cyclocitral dimethyl acetal. This corresponds to a yield of 38.5% of theory.

(C) Oxidation with tert.-butyl hydroperoxide in the presence of Cu(II) acetylacetonate 113.25 g (0.57 mole) of α-cyclocitral dimethyl acetal were dissolved in 230 ml of toluene, and 6.9 g of Cu(II) acetylacetonate were added to the solution. The resulting mixture was heated at 70° C., and 283.2 ml of tert.-butyl hydroperoxide (80% strength in di-tert.-butyl peroxide) were added. After 10½ hours, the reaction mixture was cooled to room temperature, 250 ml of water were added and the mixture was then stirred for 30 minutes. The phases were separated, and the organic phase was stirred for 1 hour with 200 ml of saturated sodium sulfite solution. The aqueous phases were combined, and extracted with 100 ml of hexane, and the hexane phase, together with the organic phase, was dried over MgSO$_4$ and then evaporated down in a rotary evaporator at 45° C. The residue was distilled rapidly over a short bridge (bp. 90° C./0.05). Fine distillation gave 85.5 g (70.7% of theory) of 3-oxo-α-cyclocitral dimethyl acetal of boiling point 80°-85° C. 0.01 mbar.

Mass spectrum: m/e=212 (M+ 0%); 181 (M—OCH$_3$; 3%); 137 (M—CH(OCH$_3$)$_2$; 3%); 75 (CH(OCH$_3$)$_2$; 100%).

$^1$H-NMR (CDCl$_3$) δ=1.046 (3H, S, C$_1$—CH$_3$); 1.12 (3H, S, C$_1$—CH$_3$); 1.974 (1H, d, J=16.5 Hz, C$_2$—Hax); 2.10 (3H, S, C$_5$—CH$_3$); 2.25 (1H, S, br, C$_6$—H); 2.61 (1H, d, J=16.5 Hz, C$_2$—Heq); 3.42 (3H, S, OCH$_3$); 3.45 (3H, S, OCH$_3$); 4.52 (1H, d, J=2.1 Hz, C$_7$—H); 5.98 (1H, S, C$_4$—H).

Example 2

Preparation of 3-hydroxy-α-cyclocitral dimethyl acetal (A) Reduction with sodium borohydride 70 g (0.33 mole) of 3-oxo-α-cyclocitral dimethyl acetal was dissolved in 600 ml of methanol, and 104.5 g of CeCl$_3$.5H$_2$O were added. The solution was cooled to 5° C., and 20 g of sodium borohydride were added, a little at a time, in the course of 1 hour. Thereafter, the mixture was brought to room temperature in the course of 30 minutes and then stirred at this temperature for a further hour. A solution of 40 g of sodium acetate in 800 ml of water was then added, and the entire reaction medium was extracted 5 times with 400 ml of methylene chloride. The organic phase was washed with 200 ml of water and dried with MgSO$_4$, and the solvent was stripped off to give 71 g (100% of theory) of a colorless oil consisting of an 80:20 mixture of the cis- and trans-isomers of 3-hydroxy-α-cyclocitral dimethyl acetal.

$^1$H-NMR cis δ=0.906 (3H, S, C$_1$—CH$_3$); 1.01 (3H, S, C$_1$—CH$_3$); 1.62 (2H, d, J=8,1 Hz, C$_2$—H$_2$); 1.68 (1H, S, br, OH); 1.84 (1H, S, br, C$_6$—H); 1.86 (3H, S, br, C$_5$—CH$_3$); 3.40 (3H, S, OCH$_3$); 3.44 (3H, S, OCH$_3$); 4.13 (1H, m, br, C$_3$—H); 4.36 (1H, d, J=2,7 Hz, C$_7$—H); 5.61 (1H, S, br, C$_4$—H).

trans δ=0.936 (3H, S, C$_1$—CH$_3$); 1.08 (3H, S, C$_1$—CH$_3$); 1.34 (1H, dd, J=6,48 Hz, J=13,5 Hz, C$_2$—H); 1.86 (3H, S, C$_5$—CH$_3$); 1.90 (1H, dd, J=6,48 Hz, J=13,5 Hz, C$_2$—H); 2.04 (1H, S, br, C$_6$—H); 3.39 (3H, S, OCH$_3$); 3.40 (3H, S, OCH$_3$); 4.23 (1H, m, br, C$_3$—H); 4.28 (1H, S, br, C$_7$—H); 5.59 (1H, S, br, C$_4$—H).

(B) Reduction with diisobutyl-aluminum hydride 1.27 g (0.005 mole) of 3-oxo-α-cyclocitral dimethyl acetal were dissolved in 30 ml of anhydrous n-hexane, and the solution was cooled to 5° C. 5 ml of a 1M solution of diisobutyl-aluminum hydride in toluene were added dropwise at this temperature under an N$_2$ atmosphere in the course of 20 minutes, and the reaction mixture was stirred for a further 30 minutes, while warming to room temperature. 70 ml of ice water were then added, while cooling in an ice bath, and the mixture was extracted with methyl tert.-butyl ether, and the organic phase was washed with water, dried with MgSO$_4$ and freed from solvent in a rotary evaporator. Yield: 0.75 g (70% of theory).

(C) Reduction with lithium tri-tert.-butoxy-aluminum hydride 2.17 g (0.01 mole) of 3-oxo-α-cyclocitral dimethyl acetal were dissolved in 30 ml of anhydrous tetrahydrofuran, and 5.08 g (0.02 mole) of lithium tri-tert.-butoxy-aluminum hydride were added to the solution. The mixture was stirred under reflux for 12 hours, after which 5 ml of methanol were added dropwise and the reaction mixture was diluted with 30 ml of water and then extracted with methylene chloride. The organic phase was washed with 10% strength ammonium chloride solution, dried and evaporated down. Yield: 1.8 g (85% of theory).

Example 3

Preparation of 3-hydroxy-α-cyclocitral 250 mg of p-toluenesulfonic acid were added to a solution of 15 g (0.07 mole) of 3-hydroxy-α-cyclocitral dimethyl acetal in 360 ml of a 65% strength aqueous acetone. After the mixture had been standing for 12 hours at room temperature, it was diluted with 800 ml of water and then extracted with 3×150 ml of diethyl ether, and the combined ether phases were washed with 100 ml of water, dried with MgSO$_4$ and evaporated down in a rotary evaporator. Yield: 10.30 g (87.5% of theory).

$^1$H-NMR cis: δ=0.952 (3H, S, C$_1$—CH$_3$); 1.03 (3H, S, C$_1$—CH$_3$); 1.5-1,95 (2H, m, C$_2$—H$_2$); 1.64 (3H, S, C$_5$—CH$_3$); 2.42 (1H, d, J=5.4 Hz, C$_6$—H); 3.08 (1H, br, OH); 4.31 (1H, t, br, J=7.2 Hz, C$_3$—H); 5.02 (1H, S, br, C$_4$—H); 9.54 (1H, d, J=5.4 Hz, C$_7$—H).

trans: δ=0.91 (3H, S, C$_1$—CH$_3$); 1.10 (3H, S, C$_1$—CH$_3$), 1.5-1.95 (2H, m, C$_2$—H$_2$), 1.64 (3H, S, C$_5$—CH$_3$); 2.60 (1H, d, br, C$_6$—H); 3.08 (1H, br, OH); 4.44 (1H, t, br, J=5,4 Hz, C$_3$—H); 5.02 (1H, S, br, C$_4$—H); 9.51 (1H, d, J=5.4 Hz, C$_7$—H).

Example 4

(a) Oxidation 33 g (0.168 mole) of α-cyclocitral ethylene glycol acetal were oxidized with 125 ml of a 2.2M tert.-butyl chromate solution in the course of 30 hours, by a method similar to that described in Example 1B. The conversion was 47%. Distillation under 0.3 mbar and at 95°-100° C. gave 12.9 g of a yellow oil which crystallized on cooling. The yield of 3-oxo-α-cyclocitral ethylene glycol acetal was 78%, based on α-cyclocitral ethylene glycol acetal converted. After recrystallization from diisopropyl ether, the melting point was 71°-71.5° C.

Mass spectrum: m/e: 224 (M+, 5%), 87

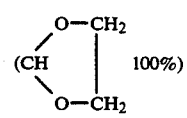

$^1$H-NMR δ=1.05 (3H, S, C$_1$—CH$_3$); 1.18 (3H, S, C$_1$—CH$_3$); 1.99 (1H, d, J=17.2 Hz, C$_2$—Hax); 2.09 (3H, S, C$_5$—CH$_3$); 2.36 (1H, d, J=2.7 Hz; C$_6$—H); 2.70 (1H, d, J=17.2, C$_2$—Hequ.); 3.76-3.94 (4H, m, C$_4'$, C$_5'$—H$_2$); 5.23 (1H, d, J=27; C—H); 5.97 (1H, Sbr; H, C$_4$—H).

(b) Reduction 3.5 g (0.016 mole) of 3-oxo-α-cyclocitral ethylene glycol acetal were reduced with 1 g of NaBH$_4$ and 5.2 g of CeCl$_3$.7H$_2$O by a method similar to that described in Example 2. The conventional working up procedure gave 3.35 g (96% of theory) of a colorless, highly viscous oil which contained 83% of trans- and 17% of cis-3-hydroxy-α-cyclocitral ethylene glycol acetal.

$^1$H-NMR for the trans-alcohol: δ=(CDCl$_3$)=0.92 (3H, S, C$_1$—CH$_3$); 1.04 (3H, S, C$_1$—CH$_3$); 1.646 (2H, d, J=8 Hz, C$_2$—H$_2$); 1.834 (3H, S, C$_5$—CH$_3$); 1.92 (1H, brS, C$_6$—H); 1.96 (1H, S, br, OH); 3.74-4.04 (4H, m, CH$_2$—CH$_2$); 4.13 (1H, br, t, J=8 Hz, C$_3$—H); 5.02 (1H, d, J=1.6 Hz, C$_4$—H); 5.62 (1H, s, br C$_5'$—H).

(c) Hydrolysis 1 g (0.0047 mole) of 3-hydroxy-α-cyclocitral ethylene glycol acetal in a mixture of 20 ml of 65% strength by volume aqueous acetone and 10 mg of p-toluenesulfonic acid was stirred at 45° C. for 12 hours, after which the reaction mixture was diluted with 40 ml of water and extracted with methyl tert.-butyl ether, and the organic phase was washed with water, dried, and evaporated down under reduced pressure.

Yield: 0.65 g (83% of theory) of 3-hydroxy-α-cyclocitral.

Example 5

(a) Oxidation 50 g (0.238 mole) of α-cyclocitral propylene glycol acetal were mixed with 50 ml of tert.-butyl hydroperoxide and 125 mg of RhCl$_3$.3H$_2$O, and the mixture was gassed with 15 liters of oxygen in the course of 3 hours at 95° C. The reaction mixture was cooled, diluted with 250 ml of methylene chloride and washed with 3×25 ml of water, the organic phase was dried with sodium sulfate and evaporated down in a rotary evaporator, and the residue was degassed under 0.63 mbar and at 90° C. and then distilled in a molecular distillation apparatus. 21.3 g of 3-oxo-α-cyclocitral propylene 1,3-glycol acetal were obtained in the form of a viscous oil, which crystallized after purification with methyl tert.-butyl ether. Mp. 63°-65.5° C.; yield 38% of theory.

Mass spectrum: m/e: 224 (M+, 5%);

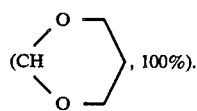

H-NMR: δ(CDCl$_3$) 1.02 (3H, S, C$_1$—CH$_3$); 1.14 (3H, S, C$_1$—CH$_3$); 1.31 (1H, d, br, J=13.5 Hz, C$_5'$—Hax); 1.95 (1H, d, J=16.5 Hz, C$_2$—Hax); 2.03 (1H, m, C$_5'$—Heq), 2.11 (3H, S, C$_5$—CH$_3$); 2.17 (1H, S, br, C$_6$—H); 2.65 (1H, d, J=16.5 Hz, C$_5$—Heq); 3.73 (2H, m, C$_6'$—H$_2$ax); 4.11 (2H, m, C'$_{4.6}$—H$_2$, eq); 4.88 (1H, d, J=2,7 Hz, C$_2'$—H); S, 97 (1H, S, br, C$_4$—H).

(b) Reduction 7.1 g (0.032 mole) of 3-oxo-α-cyclocitral propylene 1,3-glycol acetal were reacted with 1.68 g of NaBH$_4$ in the presence of 8.68 g of CeCl$_3$.7H$_2$O by a method similar to that described in Example 2A. 7.1 g (99% of theory) of 3-hydroxy-α-cyclocitral propylene 1,3-glycol acetal were obtained in the form of a cis/trans mixture (~15:85).

Mass spectrum: m/e: 226 (M+, 4%); 87

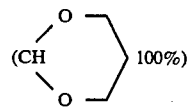

H-NMR for the trans compound: δ(CDCl$_3$) 0.896 (3H, S, C$_1$—CH$_3$); 1.03 (3H, S, C$_1$—CH$_3$); 1.31 (1H, d, br, J=13,0 Hz, C'$_5$—Hax); 1.594 (2H, d, J=8 Hz; C$_2$—H$_2$); 1.764 (1H, S, br, C$_6$—H); 1.880 (3H, S, C$_5$—CH$_3$); 1.94 (1H, S, OH); 1.95-2.14 (1H, m, C'$_5$—Heq); 3.60 (2H, dd, J=13.0 Hz, J=27 Hz, C'$_{4.6}$—H$_2$ax); 4.11 (2H, m, br, C$_{4.8}$—H$_2$eq); 4.15 (1H, m, br, C$_3$—H); 4.75 (1H, d, J=1.6 hz, C'$_1$—H); S, 626 (1H; S, br, C$_4$—H).

Example 6

(a) Oxidation 36 g (0.151 mole) of α-cyclocitral neopentylglycol acetal were oxidized with 125 ml of a 2.2 molar solution of tert.-butyl chromate by a method similar to that described in Example 1Bb. After 30 hours, 72% of the starting material had been converted. Distillation of the resulting crude product under 0.25 mbar and at 115° C. gave 16.4 g of a highly viscous oil containing 88% of 3-oxo-α- cyclocitral neopentylglycol acetal. Crystallization from diisopropyl ether gave pure 3-oxo-α-cyclocitral neopentylglycol acetal of melting point 79°-81° C. The yield was 60%, based on cyclocitral acetal converted.

H-NMR δ(CDCl$_3$): 0.70 (3H, S C'$_5$—CHeq.); 1.028 (3H, S, C$_1$—CH$_3$); 1.096 (3H, S, C'$_5$—CH$_3$ax); 1.124 (3H, S, C$_1$—CH$_3$); 1.94 (1H, d, J=17.8 Hz; C$_2$—Hax); 2.136 (3H, S, C$_5$—CH$_3$); 2.67 (1H, d, J=17.8 Hz, C$_2$—Heq); 3.4 (1H, d, J=10 Hz; C'$_{4.6}$—H); 3.41 (1H, d, J=10 Hz, C'$_{4.6}$—H); 3.57 (1H, d, J=10 Hz, C'$_{4.6}$—H); 3.62 (1H, d, J=10 Hz, C'$_{4.6}$—H); 4.79 (1H, S, C'$_2$—H); 5.99 (1H, s, C$_4$—H).

(b) Reduction 4.2 g (0.016 mole) of 3-oxo-α-cyclocitral neopentylglycol acetal were reduced with 1 g of NaBH$_4$ and 5.2 g of CeCl$_3$.7H$_2$O by a method similar to that described in Example 2A. Working up in the conventional manner gave 4.0 g (95% of theory) of 3-hydroxy-α-cyclocitral neopentylglycol acetal in the form of a colorless, highly viscous oil.

$^1$H-NMR δ(CDCl$_3$)=0.706 (3H, S, C'$_5$—CH$_3$eq); 0.90 (3H, S, C$_1$—CH$_3$); 1.026 (3H, S, C$_1$—CH$_3$); 1.16 (3H, S, C'$_5$—CH$_3$ax); 1.592 (2H, d, br, J=8.6 Hz, C$_2$—H$_2$); 1.82 (1H, S, C$_6$—H); 1.86 (1H, S, br, OH); 1.90 (3H, S, C$_5$—CH$_3$); 3.40 (2H, d, br, J=10.8 Hz, C'$_{2.6}$—H$_2$); 3.62 (2H, d, J=10.8 Hz, C'$_{4.6}$—H$_2$); 4.11 (1H, t, br, J=8.6 Hz, C$_3$-H); 4.62 (1H, d, J=1.5, C'$_2$—H); 5.608 (1H, S, br, C$_4$—H).

Example 7

Use of 3-hydroxy-α-cyclocitral for the preparation of 3-acetoxy-β-ionone

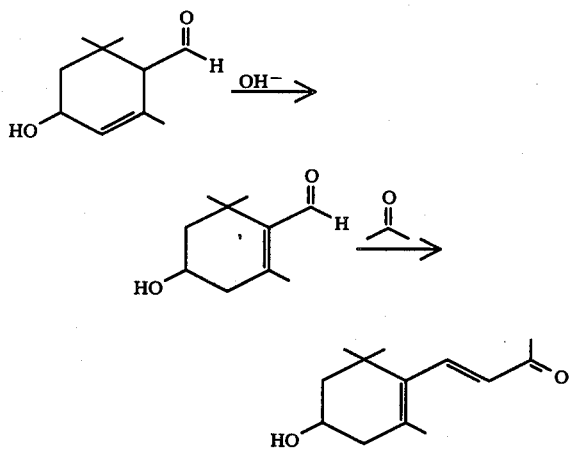

10.3 g (0.061 mole) of 3-hydroxy-α-cyclocitral were diluted with 5 ml of acetone, and 8.5 g of NaOH pellets were added. The mixture was stirred for one minute, after which 250 ml of acetone were added and stirring was continued for a further 3 hours at room temperature. Thereafter, 750 ml of water and 100 ml of CH$_2$Cl$_2$ were added to the reddish brown reaction mixture, and the aqueous phase was extracted with 3×100 ml of CH$_2$Cl$_2$. The combined organic phases were washed with 100 ml of 0.2N HCl and 100 ml of water, dried with MgSO$_4$ and evaporated down in a rotary evaporator under 15 mbar and at 40° C. to give 25.5 g of a honey-colored oil containing 48.7% of 3-hydroxy-β-ionone; This corresponds to a yield of 97% of theory.

The oil obtained was dissolved in 140 ml of pyridine, and 28 ml of acetic anhydride were added. 50 mg of 4-dimethylaminopyridine were added, after which the mixture was left to stand at room temperature for 16 hours. It was then diluted with 500 ml of water, brought to pH 3 with dilute hydrochloric acid and extracted with 200 ml of CH$_2$Cl$_2$, and the extract was washed twice with 50 ml of water, once with 50 ml of saturated NaHCO$_3$ solution and once with 50 ml of water, dried over MgSO$_4$ and evaporated down in a rotary evaporator to give 16.23 g of 89% pure 3-acetoxy-β-ionone. This corresponds to a yield of 94% of theory, based on 3-hydroxy-α-cyclocitral employed.

Comparative Example 11.9 g (0.06 mole) of 2,2,6-trimethylcyclohexane-1-carbaldehyde dimethyl acetal were oxidized by a method similar to that described in Example 1A. After 2 hours, the starting material was no longer detectable by gas chromatography. The product obtained was washed twice with 30 ml of water, the combined water phases were extracted 3 times with 30 ml of methyl tert.-butyl ether, and the organic phases were combined, dried with MgSO$_4$ and evaporated down in a rotary evaporator.

Crystallization from pentane gave colorless crystals of melting point 87°–90° C.

NMR δ=0.9 (3H, d, J=5.4 Hz, C$_5$—CH$_3$); 1,00 (3H, S, C$_1$—CH$_3$); 1.05 (3H, S, C$_1$—CH$_3$); 1.08–1.27 (m); 1.36–1.59 (m); 1.68–1.9 (m); 11.0–11.3 (1H, S, br, CO$_2$H).

Mass spectrum: m/e: 170 (M+, 40%); 152 (68%); 110 (100%).

The product obtained is not 3-oxo-2,2,6-trimethylcyclohexane-1-carbaldehyde dimethyl acetal but 2,2,6-trimethylcyclohexane-1-carboxylic acid.

Example 8

(a) A solution of 200 mg (0.89 millimole) of (±)-3-oxo-α-cyclocitral propylene glycol acetal in 2 ml of ethanol was poured onto a glass column (diameter=25.4 mm, length=1,090 mm) filled with 220 g of cellulose triacetate (prepared in accordance with Houben-Weyl, Methoden der organischen Chemie, 4th Edition, Volume 14/2, page 875, line 5 et seq.), and elution was carried out with 96% strength ethanol (flow rate 65 ml/hour, p=3.5 bar). The eluate was fractionated so that about 25% of the amount used formed a fraction containing dextrorotatory antipodes, about 50% formed a middle racemate-containing fraction and about 25% formed a fraction containing levorotatory antipodes. The eluting agent was evaporated off in a rotary evaporator, and the optically active ketones were obtained with an optical purity of 98–100%.

(+)-(6S)-3-oxo-α-cyclocitral propylene glycol acetal [α]$_D^{20}$=+147.6° (c=1; CHCl$_3$).

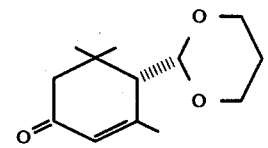

(−)-(6R)-3-oxo-α-cyclocitral propylene glycol acetal [α]$_D^{20}$=−152.9° (c=1; CHCl$_3$).

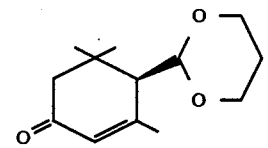

The following optically active ketones of the formula I were obtained by a method similar to that described in Example 1a:

(b) (+)-(6S)-3-oxo-α-cyclocitral dimethyl acetal [α]$_D^{20}$=+179.0° (c=1; CHCl$_3$).
(−)-(6R)-3-ixi-α-cyclocitral dimethyl acetal [α]$_D^{20}$=−177.2 (c=1; CHCl$_3$).
(c) (+)-(6S)-3-oxo-α-cyclocitral ethylene glycol acetal [α]$_D^{20}$=+141.4° (c=0.4; CH$_3$OH).
(−)-(6R)-3-oxo-α-cyclocitral ethylene glycol acetal [α]$_D^{20}$=−139.7° (c=0.4; CH$_3$OH).
(d) (+)-(6S)-3-oxo-α-cyclocitral neopentylglycol acetal [α]$_D^{20}$=+49.2° (c=1; CHCl$_3$).
(−)-(6R)-3-oxo-α-cyclocitral neopentylglycol acetal [α]$_D^{20}$=−48.0° (c=1; CHCl$_3$).

Example 9

Reracemization of the optically active ketone which is not required 50 mg of sodium methylate were added to a solution of 300 mg of (+)-3-oxo-α-cyclocitral propylene glycol acetal in 5 ml of methanol, after which the mixture was heated at 40° C. for 3 hours. Thereafter, 2 ml of a 10% strength aqueous NH$_4$Cl solution were added to the reaction mixture, which was then extracted with methyl tert.-butyl ether. Drying with Na$_2$SO$_4$ and evaporating the solvent gave a pale yellow oil whose spectroscopic data were identical to those of the starting compound. The optical rotation was still $[\alpha]_D^{20} = +7°$.

The resulting racemic 3-oxo-α-cyclocitral propylene glycol acetal can be used again for the preparation of (+)- or (−)-3-oxo-α-cyclocitral propylene glycol acetals by the method described in Example 1a.

Example 10

(a) Preparation of optically active cis- and trans-(6S)-3-hydroxy-α-cyclocitral propylene glycol acetal 4 g of CeCl.7H₂O were added to a solution of 2.1 g (9 millimoles) of (+)-(6S)-3-oxo-α-cyclocitral propylene glycol acetal in 40 ml of methanol, the solution was cooled to −5° C. and 400 mg of NaBH₄ were added a little at a time, while stirring. The reaction mixture was stirred for a further hour at −5° C., then brought to room temperature in the course of 0.5 hour and kept at this temperature for a further hour. After decomposition with a solution of 1.2 g of sodium acetate in 20 ml of water, the mixture was extracted with 5×15 ml of methylene chloride, the organic phase was washed with 15 ml of water and dried with MgSO₄, and the solvent was evaporated off to give 2.10 g (100% of theory) of a colorless oil consisting of a 15:85 mixture of the cis- and trans-isomers of 3-hydroxy-α-cyclocitral propylene glycol acetal. The diastereomeric 3-hydroxyacetals were separated by column chromatography over silica gel.

(+)-cis-(3R,6S)-3-hydroxy-α-cyclocitral propylene glycol acetal
$[\alpha]_D^{20} = +115.8$ (c=0.3; CH₃OH).

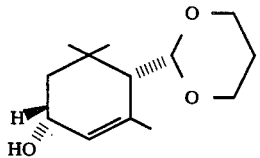

(+)-trans-(3S,6S)-3-hydroxy-α-cyclocitral propylene glycol acetal
$[\alpha]_D^{20} = +100.8$ (c=1.0; CH₃OH).

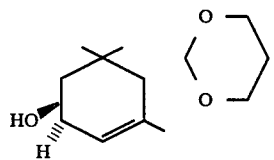

The optically active 3-hydroxy-α-cyclocitral acetals below were also prepared by a method similar to that described in Example 3a.

(b) (−)-trans-(3R,6R)-3-hydroxy-α-cyclocitral neopentylglycol acetal
$[\alpha]_D^{20} = -65.4°$ (c=1; CH₃OH).

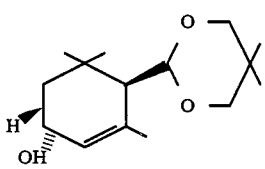

(+)-trans-(3R,6R)-3-hydroxy-α-cyclocitral neopentylglycol acetal
$[\alpha]_D^{20} = +64.8°$ (c=1; CH₃OH).

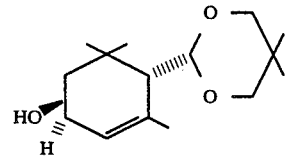

(c) (−)-trans-(3S,6S)-3-hydroxy-α-cyclocitral ethylene glycol acetal
$[\alpha]_D^{20} = 131.5°$ (c=1; CH₃OH).

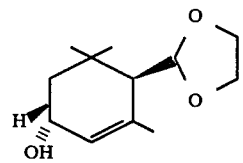

(+)-trans-(3R,6R)-3-hydroxy-α-cyclocitral ethylene glycol acetal
$[\alpha]_D^{20} = +131.2°$ (c=1; CH₃OH)

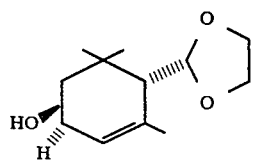

Example 11

Preparation of (+)-trans-(3S,6S)-3-hydroxy-α-cyclocitral 10 mg of p-toluenesulfonic acid were added to a solution of 500 mg (2.2 millimoles) of (+)-trans-(3S,6S)-3-hydroxy-α-cyclocitral propylene glycol acetal in 10 ml of 65% strength aqueous acetone, and the reaction mixture was left to stand at room temperature for 12 hours. Thereafter, it was diluted with 25 ml of water and extracted with 3×5 ml of methyl tert.-butyl ether. The combined ether phases were washed with 2 ml of water, dried with MgSO₄ and evaporated down in a rotary evaporator to give 295 mg (80% of theory) of product. $[\alpha]_D^{20} = +421°$ (c=0.5; CH₃OH).

Example 12

Preparation of (−)-(3S)-3-hydroxy-β-cyclocitral 0.3 ml of 2% strength KOH was added to a solution of 540 mg (3.2 millimoles) of (+)-trans-(3S,6S)-3-hydroxy-α-cyclocitral in 1.5 ml of ethanol at room temperature. The mixture was stirred for one hour, after which 20 ml of CH₂Cl₂ were added, and the organic phase was washed first with 2 ml of saturated NH₄CL solution and then with H₂O, dried with MgSO₄ and evaporated down to give 450 mg of a pale yellow oil containing 9.3% of starting material in addition to 90.7% of the desired product. $[\alpha]_D^{20} = -34.8°$ (c=0.85, CH₃OH).

The corresponding optical antipodes of the compounds prepared as described in Examples 3, 4 and 5 are obtained if the appropriate (−)-3-oxo-α-cyclocitral acetal is used as the starting material for the further reaction.

We claim:

1. A 3-hydroxy-α-cyclocitral of the formula I

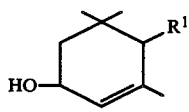

wherein R¹ is

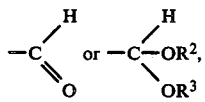

$R^2$ and $R^3$ can be identical or different and are each a straight-chain or branched alkyl group of 1 to 6 carbon atoms, or $R^2$ and $R^3$ together form an ethylene or propylene group which can be substituted by methyl or ethyl.

2. Optically active α-cyclocitral of the formulae A or B

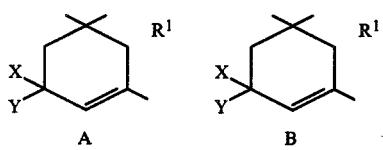

wherein R¹ is

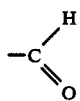

if X is hydrogen and Y is OH, but is otherwise

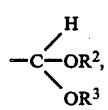

$R^2$ and $R^3$ can be identical or different and are each a straight-chain or branched alkyl group of 1 to 6 carbon atoms, or $R^2$ and $R^3$ together form an ethylene or propylene group which can be substituted by methyl or ethyl, and X and Y together are oxygen, or X is hydrogen if Y is OH.

3. Optically active 3-hydroxy-α-cyclocitral of the formulae A and B as claimed in claim 2, wherein X is hydrogen if Y is OH.

4. Optically active 3-oxo-α-cyclocitral of the formula A and B (A III and B III) as claimed in claim 2, wherein X and Y together are oxygen.

5. The α-cyclocitral of claim 4, having the formula:

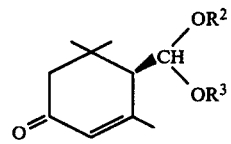

6. The α-cyclocitral of claim 4, having the formula:

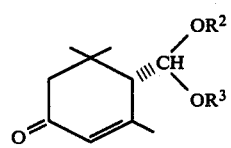

7. The α-cyclocitral of claim 3, having the formula:

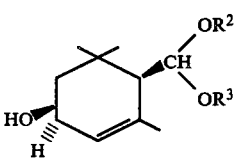

8. The α-cyclocitral of claim 3, having the formula:

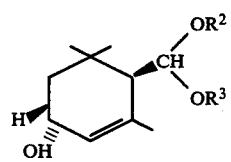

9. The α-cyclocitral of claim 3, having the formula:

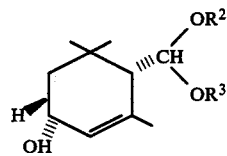

10. The α-cyclocitral of claim 3, having the formula:

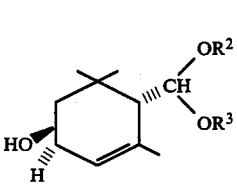

11. The α-cyclocitral of claim 3, having the formula:

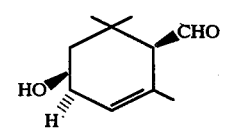

12. The α-cyclocitral of claim 3, having the formula:

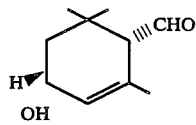
13. The α-cyclocitral of claim 3, having the formula:
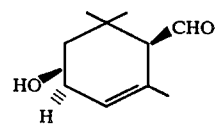
14. The α-cyclocitral of claim 3, having the formula:
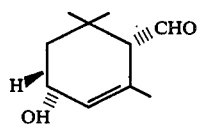
15. The α-cyclocitral of claim 1, wherein $R^2$ and $R^3$ are methyl.
16. The α-cyclocitral of claim 1, wherein $R^2$ and $R^3$ together form $-CH_2CH_2-$.
17. The α-cyclocitral of claim 1, wherein $R^2$ and $R^3$ together form $-CH_2CH_2CH_2-$.
* * * * *